United States Patent
Skinner et al.

(10) Patent No.: US 6,477,428 B1
(45) Date of Patent: Nov. 5, 2002

(54) ENDOCARDIAL LEAD WITH VINYLIDENE FLUORIDE INSULATION

(75) Inventors: Dwight Skinner, St. Anthony; Stuart R. Chastain, Shoreview; Mohan Krishnan, St. Paul; Chris Zerby, New Brighton, all of MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/514,811

(22) Filed: Feb. 28, 2000

(51) Int. Cl.[7] .................................................. A61N 1/05
(52) U.S. Cl. ........................ 607/122; 607/116; 600/374
(58) Field of Search ................................. 607/122, 115, 607/116, 121, 123; 600/372, 373, 374, 377, 395

(56) References Cited

U.S. PATENT DOCUMENTS

| | | | |
|---|---|---|---|
| 5,324,321 A | * 6/1994 | Pohndorf et al. | 607/116 |
| 5,539,052 A | * 7/1996 | Shieh et al. | 525/177 |
| 5,628,774 A | 5/1997 | Helland et al. | 607/116 |
| 5,796,044 A | * 8/1998 | Cobian et al. | 174/103 |
| 5,947,964 A | * 9/1999 | Eggers et al. | 606/41 |
| 5,968,087 A | * 10/1999 | Hess et al. | 600/372 |
| 6,141,594 A | * 10/2000 | Flynn et al. | 600/374 |

OTHER PUBLICATIONS

"High Performance Custom Coating and Surface Modification Services", Materials and Techniques information published by Vitek Research Corporation at http://www.ncia,net/vitek/material.htm., pp. 1–9 (1996).

Kleinhanz, P., et al., "Comparing Insulating Materials for Electrosurgical Instruments", *Medical Device & Diagnostic Industry*, vol. 18, No. 2, pp. 82, 84–86 and 88 (Feb. 1996).

* cited by examiner

Primary Examiner—Kennedy Schaetzle
(74) Attorney, Agent, or Firm—Schwegman, Lundberg, Woessner & Kluth, P.A.

(57) ABSTRACT

A lead has a flexible lead body which extends from a proximal end to a distal end. The lead body has a conductor coupled with an electrode. At least a portion of the flexible lead body includes a polymer of vinylidene fluoride, or a polymer of vinylidene fluoride and silicone rubber. The polymer of vinylidene fluoride includes, but is not limited to, a homopolymer, a copolymer, or a terpolymer.

18 Claims, 3 Drawing Sheets

ENDOCARDIAL LEAD WITH VINYLIDENE FLUORIDE INSULATION

FIELD OF THE INVENTION

The present invention relates generally to leads implanted in the heart and for conducting electrical signals to and from the heart. More particularly, it pertains to insulation for an endocardial lead.

BACKGROUND OF THE INVENTION

Leads implanted in or about the heart have been used to reverse certain life threatening arrhythmias, or to stimulate contraction of the heart. Electrical energy is applied to the heart via the leads to return the heart to normal rhythm. Leads have also been used to sense in the atrium or ventricle of the heart and to deliver pacing pulses to the atrium or ventricle.

Cardiac pacing may be performed by the transvenous method or by leads implanted directly onto the ventricular epicardium. Permanent transvenous pacing is performed using a lead positioned within one or more chambers of the heart. A lead may be positioned in the ventricle or in the atrium through a subclavian vein, and the lead terminal pins are attached to a pacemaker which is implanted subcutaneously.

Leads provide the electrical connection between the pulse generator and the heart tissue which is to be excited. Since the lead is disposed in body fluid and is disposed within the patient for long periods of time, electrical insulation of the lead is important. One approach to providing electrical insulation is to provide a lead body of silicone. However, the silicone provides limited abrasion resistance. During placement of the lead, the tip of the lead and lead body travels intravenously through veins and the heart. While traveling through the veins, the lead body may experience resistance from the lead body rubbing against the wall of the vein or the helix at the tip of the lead may snag or attach to the side wall of the vein. This is undesirable as it may cause damage or other complications to a patient during implantation of the lead. In addition, for leads having multiple legs or when multiple leads are implanted, it is important that the lead bodies do not adhere to one another after placement of the lead within the patient.

Accordingly, there is a need for a lead which allows for positioning through a passage, such as a vein or artery, without substantial resistance from the wall of the vein or artery. What is also needed is a lead with improved abrasion resistance, which also provides electrical insulation for the lead.

SUMMARY OF THE THE INVENTION

A lead has a flexible lead body which extends from a proximal end to a distal end. The distal end of the lead body includes one or more legs. Optionally, the lead is coupled with a pulse generator. The lead body has a conductor coupled with an electrode. At least a portion of the flexible lead body includes polymers of vinylidene fluoride, or polymers of vinylidene fluoride and silicone rubber in multiple layers. Optionally, the polymers of vinylidene fluoride comprises a homopolymer, a copolymer, or a terpolymer. The poly (vinylidene fluoride), in one embodiment, comprises a heat shrunk layer of insulation.

A method includes increasing the abrasion resistance of a lead assembly having a flexible lead body and at least one electrode. The method includes applying a layer of poly vinylidene fluoride on the flexible lead body. Optionally, applying the layer of poly vinylidene fluoride includes heat shrinking a tube of poly vinylidene fluoride on the flexible lead body. In another embodiment, the method further includes applying a second layer of insulation, wherein the second layer of insulation is silicone rubber.

The lead and method provides abrasion resistance, lubricity, and resistance to body fluids. In addition poly vinylidene fluoride has a heat shrink temperature which does not damage the lead and does not degrade a layer of silicone on the lead.

These and other embodiments, aspects, advantages, and features of the present invention will be set forth in part in the description which follows, and in part will become apparent to those skilled in the art by reference to the following description of the invention and referenced drawings or by practice of the invention.

The aspects, advantages, and features of the invention are realized and attained by means of the instrumentalities, procedures, and combinations particularly pointed out in the appended claims and their equivalents.

DESCRIPTION OF THE EMBODIMENTS

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the spirit and scope of the present invention. Therefore, the following detailed description is not to be taken in a limiting sense, and the scope of the present invention is defined by the appended claims and their equivalents.

Figure 1:
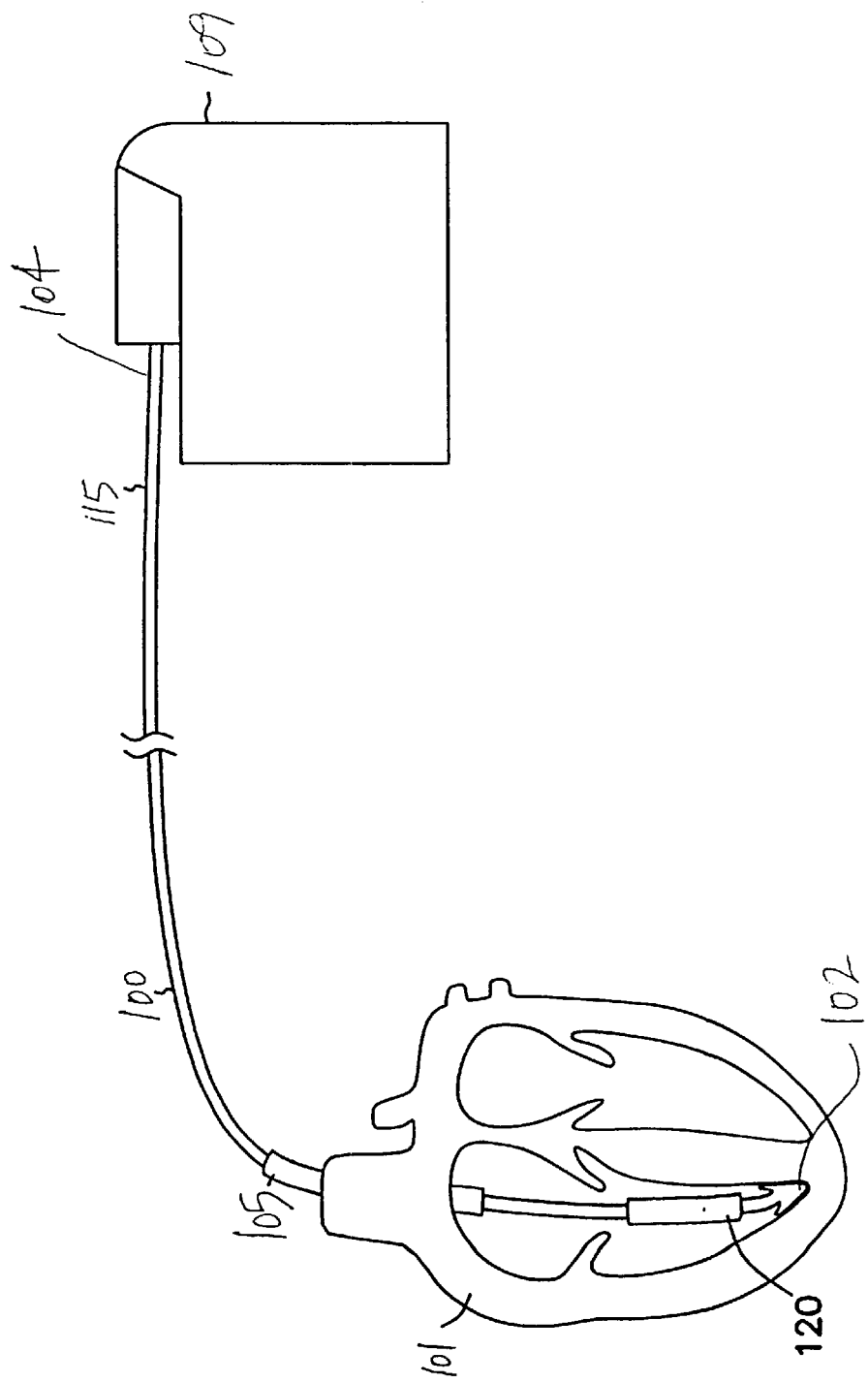
FIG. 1 illustrates a system for monitoring and stimulating the heart constructed in accordance with one embodiment.
Figure 2:
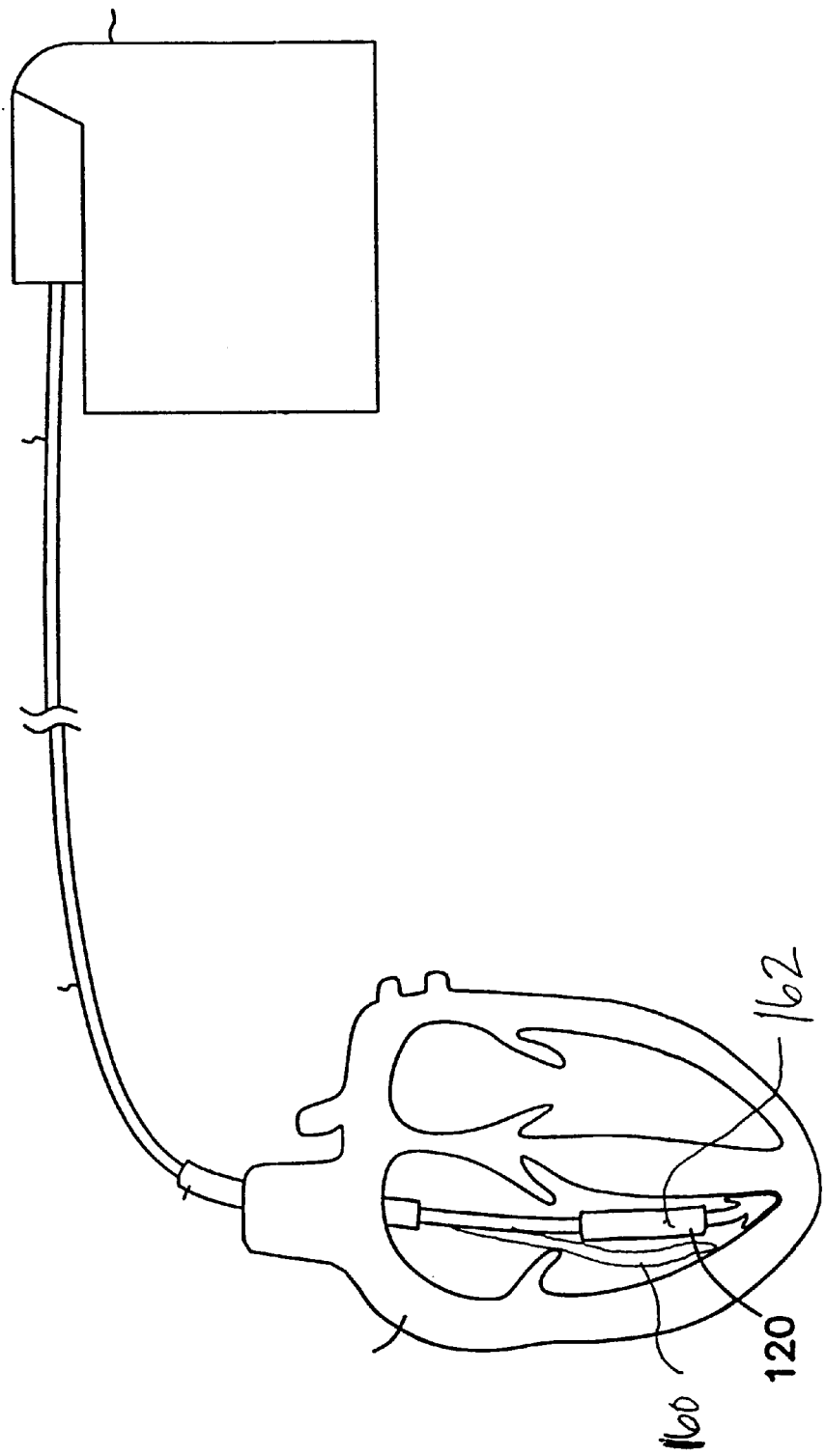
FIG. 2 illustrates a system for monitoring and stimulating the heart constructed in accordance with one embodiment.

FIG. 1 illustrates a single-pass lead 100 for delivering electrical pulses to stimulate a heart 101 and/or for receiving electrical pulses to monitor the heart 101. The lead 100 extends from a distal end 102 to a proximal end 104, and has an intermediate portion 105 therebetween. The distal end 102 is adapted for implantation within the heart of a patient, the proximal end 104 has a terminal connector which electrically connects the various electrodes and conductors within the lead body to a pulse generator and signal sensor 109. The pulse generator and signal senor 109 contains electronics to sense various electrical signals of the heart and also produce current pulses for delivery to the heart 101. As shown in FIG. 2, the lead 100 optionally includes a first leg 160 and a second leg 162 at the distal end 102 of the lead 100.

Figure 3:
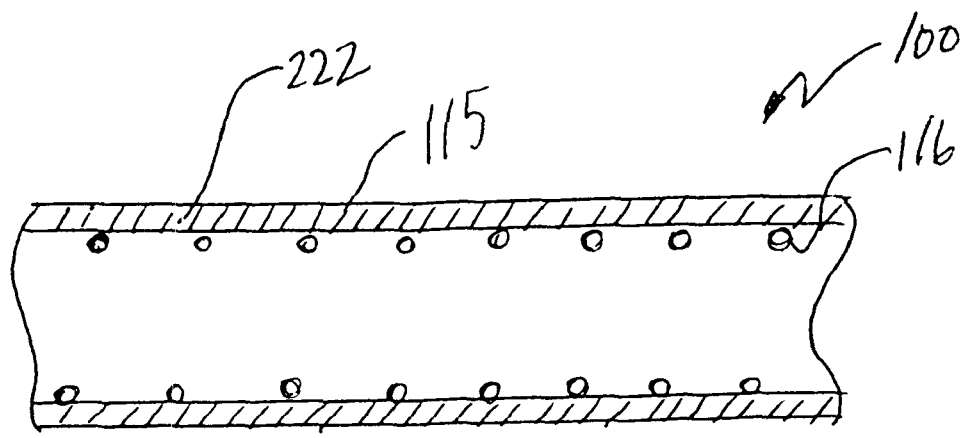
FIG. 3 is a cross-section of a lead assembly constructed in accordance with one embodiment.
Figure 4:
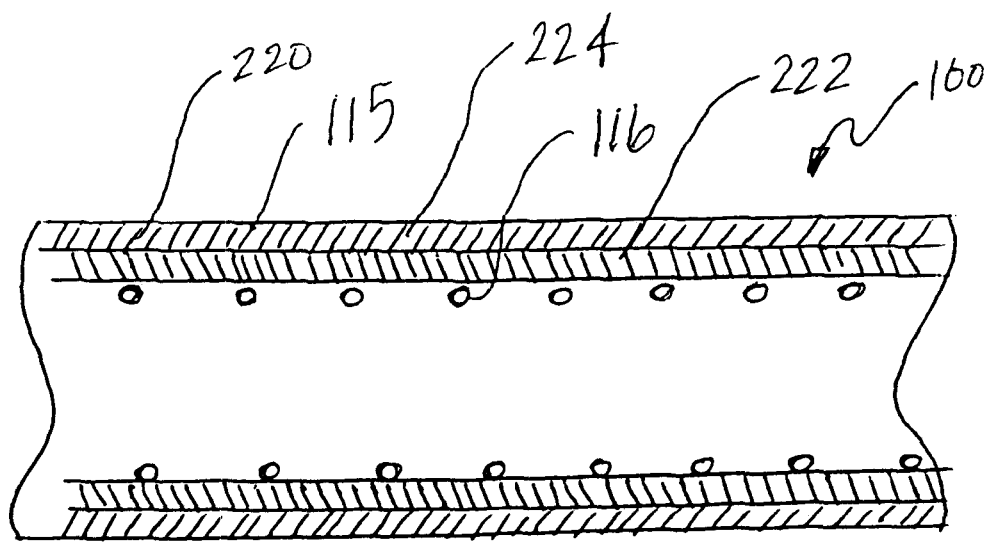
FIG. 4 is a cross-section of a lead assembly constructed in accordance with another embodiment.

The lead 100 includes a lead body 115, an elongate conductor 116 (FIGS. 3 and 4) contained within the lead body 11 5, and at least one electrode 120 coupled with the lead 100. The at least one electrode 120 is electrically coupled with the elongate conductor 116 (FIGS. 3 and 4). The lead body 115 is covered with a biocompatible insulating material 222 (FIGS. 3 and 4), discussed further below. The elongate conductor 116 defines a lumen therein and thereby is adapted to receive a stiffening stylet that extends through the length of the lead 100. The stylet is used to stiffen the lead 100, and is manipulated to facilitate the insertion of the lead 100 into and through a vein and through an intracardiac valve to advance the distal end 102 of the lead 100 into, for example, the ventricle of the heart 101. A stylet knob is coupled with the stylet for rotating the stylet, advancing the conductor into tissue of the heart, and for manipulating the lead 100.

In one embodiment, the at least one electrode 120 is disposed proximate to the distal end 102 of the lead 100. The distal end 102 of the lead 100, in one embodiment, is disposed within a ventricle of a heart, and the at least one electrode 120 delivers ventricular therapy. The at least one electrode 120 comprises, in one embodiment, a pacing and/or sensing electrode. In yet another embodiment, the at least one electrode 120 is disposed at the intermediate portion 105 between the distal end 102 and the proximal end 104 of the lead 100. In another embodiment, a plurality of electrodes 132 are disposed on the lead 100.

FIG. 2 illustrates a cross-section of the leads shown in FIGS. 1 and 2, including the lead 100, and/or the lead and the pulse generator and signal sensor 109. The lead 100 is used to chronically stimulate the heart 101, such that the lead 100 is implanted on or about the heart 101 for long periods of time. As mentioned above, the lead body 115 includes a covering of insulation 220. The insulation 220, in one embodiment, comprises a polymer of vinylidene fluoride. Optionally, the vinylidene fluoride comprises a homopolymer. Alternatively, the vinylidene fluoride comprises a copolymer. In yet another alternative, the vinylidene fluoride comprises a terpolymer.

The insulation 220 includes a first layer of insulation 222, as shown in FIG. 3. Optionally, the insulation 220 comprises vinylidene fluoride which is heat shrunk on to the flexible lead body 115. In another alternative, a second layer of insulation 224, as shown in FIG. 4, is disposed over the first layer of insulation 222. The second layer of insulation 224, optionally comprises a polymer of vinylidene fluoride, and the first layer of insulation 222 optionally comprises a different layer of material, for instance, silicone rubber. It should be noted that the vinylidene fluoride comprises the variety of vinylidene fluoride as discussed above.

Advantageously, the above described lead provides abrasion resistance, lubricity, and resistance to body fluids. In addition vinylidene fluoride has a heat shrink temperature which does not damage the lead and does not degrade a layer of silicone on the lead.

It is to be understood that the above description is intended to be illustrative, and not restrictive. It should be noted that features of the various above-described embodiments may be interchanged to form additional combinations. Many other embodiments will be apparent to those of skill in the art upon reviewing the above description. The scope of the invention should, therefore, be determined with reference to the appended claims, along with the full scope of equivalents to which such claims are entitled.

What is claimed:

1. A lead assembly comprising:
   a flexible lead body extending from a proximal end to a distal end, the lead body including at least one conductor disposed therein, at least a portion of the flexible lead body comprising a polymer of vinylidene fluoride and a layer of silicone rubber, and where the polymer of vinylidene fluoride comprises an outer layer of insulation; and
   an electrode assembly including at least one electrode electrically coupled with the conductor.

2. The lead assembly as recited in claim 1, wherein the polymer of vinylidene fluoride comprises a homopolymer.

3. The lead assembly as recited in claim 1, wherein the polymer of vinylidene fluoride comprises a copolymer.

4. The lead assembly as recited in claim 1, wherein the polymer of vinylidene fluoride comprises a terpolymer.

5. The lead assembly as recited in claim 1, wherein the polymer of vinylidene fluoride comprises a heat shrunk layer of insulation.

6. The lead assembly as recited in claim 1, wherein the lead body includes a first leg and a second leg at the distal end of the lead body.

7. A lead assembly comprising:
   a flexible lead body extending from a proximal end to a distal end, the lead body including at least one conductor disposed therein, at least a portion of the flexible lead body comprising a polymer of vinylidene fluoride that is mounted over an outside surface of another portion of the flexible lead body comprising silicone rubber; and
   an electrode assembly including at least one electrode electrically coupled with the conductor.

8. The lead assembly as recited in claim 7, wherein the polymer of vinylidene fluoride comprises a homopolymer.

9. The lead assembly as recited in claim 7, wherein the polymer of vinylidene fluoride comprises a copolymer.

10. The lead assembly as recited in claim 7, wherein the polymer of vinylidene fluoride comprises a terpolymer.

11. The lead assembly as recited in claim 7, wherein the polymer of vinylidene fluoride comprises a heat shrunk layer of insulation.

12. The lead assembly as recited in claim 7, wherein the polymer of vinylidene fluoride comprises an outer layer of insulation.

13. The lead assembly as recited in claim 7, further comprising a pulse generator electrically coupled with the electrode assembly.

14. A lead assembly comprising:
   a flexible lead body extending from a proximal end to a distal end, the lead body including at least one conductor disposed therein;
   at least a portion of the flexible lead body comprising a polymer of vinylidene fluoride, and at least a portion of the flexible lead body comprising silicone rubber, wherein the vinylidene fluoride comprises a first layer of insulation, and the silicone rubber comprising a second layer of insulation that is covered by the first layer of insulation; and
   an electrode assembly including at least one electrode electrically coupled with the conductor.

15. A method comprising:
   increasing the abrasion resistance of a lead assembly having a flexible lead body and at least one electrode, including applying a layer of silicone rubber onto the flexible lead body and applying a layer of a polymer of vinylidene fluoride onto the layer of silicone rubber.

16. The method as recited in claim 15, wherein applying the layer of a polymer of vinylidene fluoride includes heat shrinking a tube of vinylidene fluoride onto the layer of silicone rubber.

17. The method as recited in claim 15, wherein applying a layer of silicone rubber onto the flexible lead body includes applying the layer of silicone rubber onto an electrical conductor in the lead assembly.

18. The method as recited in claim 15, further comprising chronically stimulating heart tissue with the lead assembly.

* * * * *